United States Patent
Lipinski et al.

(10) Patent No.: US 11,786,446 B2
(45) Date of Patent: Oct. 17, 2023

(54) NON-OXIDATIVE HAIR DYE COMPOSITION AND METHOD

(71) Applicant: Kao Corporation, Tokyo (JP)

(72) Inventors: Normen Lipinski, Darmstadt (DE); Michael Molenda, Darmstadt (DE)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 17/634,349

(22) PCT Filed: Aug. 13, 2020

(86) PCT No.: PCT/EP2020/072743
§ 371 (c)(1),
(2) Date: Feb. 10, 2022

(87) PCT Pub. No.: WO2021/028529
PCT Pub. Date: Feb. 18, 2021

(65) Prior Publication Data
US 2022/0280399 A1    Sep. 8, 2022

(30) Foreign Application Priority Data
Aug. 14, 2019 (EP) .................................. 19191688

(51) Int. Cl.
*A61Q 5/10* (2006.01)
*A61K 8/34* (2006.01)
*A61K 8/24* (2006.01)
*A61Q 5/06* (2006.01)

(52) U.S. Cl.
CPC ............... *A61K 8/342* (2013.01); *A61K 8/24* (2013.01); *A61Q 5/065* (2013.01); *A61K 2800/432* (2013.01); *A61K 2800/5426* (2013.01); *A61K 2800/805* (2013.01); *A61K 2800/88* (2013.01)

(58) Field of Classification Search
CPC .... A61K 8/342; A61K 8/24; A61K 2800/432; A61K 2800/5426; A61K 2800/805; A61K 2800/88; A61K 8/19; A61K 8/365; A61K 8/418; A61K 8/494; A61K 8/55; A61Q 5/065

USPC .............................................. 8/405
See application file for complete search history.

(56) References Cited

U.S. PATENT DOCUMENTS

| | | |
|---|---|---|
| 2003/0066141 A1 | 4/2003 | Oshika et al. |
| 2006/0260068 A1 | 11/2006 | Legrand |
| 2007/0044251 A1* | 3/2007 | Kravtchenko ........... A61K 8/33 8/405 |
| 2015/0053230 A1 | 2/2015 | Myatt |
| 2017/0239152 A1* | 8/2017 | Goutsis ................... A61K 8/24 |
| 2018/0028435 A1 | 2/2018 | Punsch et al. |
| 2018/0289604 A1 | 10/2018 | Goutsis et al. |
| 2020/0188262 A1 | 6/2020 | Noecker et al. |

FOREIGN PATENT DOCUMENTS

| | | |
|---|---|---|
| DE | 10 2016 202 649 A1 | 8/2017 |
| DE | 10 2017 206 087 A1 | 10/2018 |
| EP | 1 238 649 A2 | 9/2002 |
| EP | 2 022 470 A1 | 2/2009 |
| EP | 3 275 422 A1 | 1/2018 |
| EP | 3 342 464 A1 | 7/2018 |
| EP | 3 427 720 A1 | 1/2019 |
| WO | WO 2018/087203 A1 | 5/2018 |

OTHER PUBLICATIONS

International Search Report and Written Opinion dated Oct. 15, 2020 in PCT/EP2020/072743 filed Aug. 13, 2020, 11 pages
Extended European Search Report dated Feb. 10, 2020 in European Patent Application No. 19191688.1 filed Aug. 14, 2019, 9 pages
Mintel, "Hair Color Supplement", Kao Corporation, 5730273, 2018, http://www.gnpd.com, pp. 1-4.
Mintel, "Anti-Brassiness Hair Colour Supplement", Kao, 4854927, 2017, http://www.gnpd.com, pp. 1-3.

* cited by examiner

*Primary Examiner* — Eisa B Elhilo

(74) *Attorney, Agent, or Firm* — Oblon, McClelland, Maier & Neustadt, L.L.P.

(57) ABSTRACT

The present invention is directed to a non-oxidative dyeing composition, method, and use for hair. The composition comprises certain direct dyes, fatty alcohols, surfactants, and a buffer system.

19 Claims, No Drawings

NON-OXIDATIVE HAIR DYE COMPOSITION AND METHOD

FIELD OF THE INVENTION

The present invention relates to a non-oxidative hair dye composition, a method for non-oxidative hair dyeing, and a use for enhancing uptake of certain types of hair direct dyes into hair.

BACKGROUND OF THE INVENTION

Nowadays, customers of cosmetic industry desire products to change the color of their hair without conferring damage to hair and without having to visit a hair dresser salon for long period of time. However, simultaneously a bright, shiny, long-lasting, and homogenous hair coloring is desired. For quickly changing hair color, typically, hair direct dyes are common means to satisfy the customer. However, in many cases the color result is not satisfactory to the customer. The prior art has attempted to solve these issues.

DE102017206087 and DE102016202649 disclose buffer systems for anionic direct dyes having a pH below 6 and a two-step hair treatment process. In contrast to these disclosures, the present invention makes use of different pH ranges and employs a one-step treatment of a ready-to-use composition.

WO2018087203 discloses hair direct dye compositions being admixed to oxidative and non-oxidative second compositions at pH ranges below 4 or above 9. However, for enhancing the non-oxidative dyeing purposes of the present invention, a different pH is required as well as a buffer system.

Mintel #5730273 and #4854927 disclose hair dyeing products comprising hair direct dyes, surfactants, and fatty alcohols, but the products do not employ a buffer system according to the present invention.

SUMMARY OF THE INVENTION

Inventors of the present invention have unexpectedly found out that a composition comprising surfactants, fatty alcohols, and a buffer system in a pH range between 6 and 8.5 enhance the uptake of hair direct dyes into hair. Despite the numerous attempts of the prior art, none of the disclosures possess the features and technical effect of the present invention. The present invention leads to intense, bright, shiny, durable, and homogenous hair color, which can be quickly applied to hair.

Thus, the first object of the present invention is a non-oxidizing hair dye composition having a pH in the range of 6 to 8.5 and comprising:

a) one or more surfactant(s), preferably selected from anionic surfactants, amphoteric/zwitterionic surfactants, and/or non-ionic surfactants, and/or their mixtures,
b) one or more fatty alcohol(s) having a linear or branched, saturated or unsaturated $C_{12}$-$C_{22}$ hydrocarbon chain, and/or their mixtures,
c) one or more hair direct dyes selected from anionic and/or non-ionic hair direct dyes, and/or their mixtures,
d) one or more buffer system(s) having a buffer capacity in the range of 0.002 g equiv/L to 0.5 g equiv/L at a pH range between 6 and 8.5, the buffer capacity being measured by acid/base titration of the composition being diluted 1:10 by volume with water at 25° C. under atmospheric conditions.

The second object of the present invention is a method of making a non-oxidative hair coloring composition comprising the steps of:
i) providing a first composition comprising one or more hair direct dyes selected from anionic and/or non-ionic direct dyes according to compound c) as defined above,
ii) providing a second composition comprising
  one or more surfactant(s) according to compounds a) as defined above,
  one or more fatty alcohols according to compound b) as defined above,
  one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above,
iii) mixing the compositions of steps i) and ii) to yield a ready-to-use composition having a pH in the range of 6 to 8.5.

The third object of the present invention is a use of a composition comprising
  one or more surfactant(s) according to compounds a) as defined above,
  one or more fatty alcohols according to compound b) as defined above,
  one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above,
for enhancing uptake of anionic and/or non-ionic direct dyes according to compound c) as defined above into hair.

Another object of the present invention is a method for non-oxidative hair coloring comprising the steps of:
iv) applying the ready-to-use mixture as defined above onto hair for a time period of 1 min to 60 min,
v) optionally rinsing off the hair.

Yet another object of the present invention is a two-part non-oxidative dyeing composition having a part A comprising one or more anionic and/or non-ionic dyes as defined above as compound c), and a part B comprising
  one or more surfactant(s) according to compounds a) as defined above,
  one or more fatty alcohols having a linear or branched, saturated or unsaturated $C_{12}$-$C_{22}$ hydrocarbon chain according to compound b) as defined above,
  one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above.

Yet another object of the present invention is a kit-of-parts comprising two compositions kept separate until directly prior to use, wherein the first separate composition comprises one or more anionic and/or non-ionic dyes as defined above as compound c), and the second separate composition comprises
  one or more surfactant(s) according to compounds a) as defined above,
  one or more fatty alcohols according to compound b) as defined above, one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above.

DETAILED DESCRIPTION OF THE INVENTION

The present invention increases deposition of anionic and/or non-ionic hair direct dyes into hair fibers. Without being bound by any theory, it is believed that the buffered composition provides for a formulation vehicle, which can stably host the hair direct dyes in solution, and allows for harvesting the affinity of the dyes to hair. In particular, the buffer system facilitates uptake of the dyes into the hair fiber.

Compounds According to a)

The composition according to the present invention comprises one or more surfactant(s), preferably selected from, anionic, cationic, amphoteric/zwitterionic, and/or non-ionic surfactants, and/or their mixtures, more preferably selected from anionic surfactants, amphoteric/zwitterionic surfactants, and/or non-ionic surfactants, and/or their mixtures.

Suitable anionic surfactants include alkylbenzene sulfonate salts, alkyl or alkenyl ether sulfate salts, alkyl or alkenyl sulfate salts, olefin sulfonate salts, alkane sulfonate salts, saturated or unsaturated fatty acid salts, alkyl or alkenyl ether carboxylate salts, α-sulfo fatty acid salts, N-acylamino acid, phosphoric acid mono-or diesters and sulfosuccinic acid esters. Examples of anionic surfactants are sodium cetearyl phosphate and sodium lauryl sulfate.

Suitable cationic surfactants include monoalkyl trimethyl ammonium chloride, dialkyl dimethyl ammonium chloride and monoalkyl trimethyl ammonium bromide. Examples of cationic surfactants are cetrimonium chloride and behentrimonium chloride.

Suitable nonionic surfactants include polyoxyalkylene alkyl ethers, polyoxyalkylene alkenyl ethers, higher fatty acid sucrose esters, polyglycerin fatty acid esters, higher fatty acid mono- or di-ethanolamides, polyoxyethylene hydrogenated castor oils, polyoxyethylene sorbitan fatty acid esters, polyoxyethylene sorbitol fatty acid esters, alkyl saccharides, alkylamine oxides and alkylamidoamine oxides. Examples of non-ionic surfactants are Ceteareth-30 and PEG-40 hydrogenated castor oil.

Suitable amphoteric surfactants include imidazolines, carbobetaines, amidobetaines, sulfobetaine, hydroxysulfobetaines and amidosulfobetaines. Examples of amphoteric surfactants are cocoyl betaine and cocoamidopropyl betaine.

It is preferred from the viewpoint of conferring color intensity to hair that the surfactant of a) is an anionic surfactant(s).

The most preferred anionic surfactant from the viewpoint of emulsion stabilization as well as conferring color intensity to hair is sodium cetearyl phosphate.

In principle, the composition of the present invention may comprise one or more cationic surfactant and/or cationic polymer. However, it is preferred from the viewpoint of conferring color intensity to hair that the total equivalent molar ratio of cationic surfactant and/or cationic polymer to one or more hair direct dyes according to compounds c) is 15 or less, preferably 10 or less, more preferably 5 or less.

In summary, the preferred aspect is to have an excess of molar concentration of dyes in contrast to cationic surfactants and/or polymers, from the viewpoint of enhancing color intensity.

In a more preferred aspect of the present invention, the composition according to the present invention is free of cationic polymers and/or cationic surfactants, from the viewpoint of enhancing color intensity.

It is preferred that the total concentration of compounds a) is 0.1% by weight or more, preferably 0.2% by weight or more, more preferably 0.3% by weight or more, calculated to the total of the composition, from the viewpoint of composition stability.

It is preferred that the total concentration of compounds a) is 10% by weight or less, preferably 8% by weight or less, more preferably 5% by weight or less, further more preferably 3% by weight or less, calculated to the total of the composition, from the viewpoint of cost of goods.

For attaining the above-mentioned effects, preferably the total concentration of compounds a) is in the range of 0.1% to 10% by weight, preferably in the range of 0.2% to 8% by weight, more preferably in the range of 0.3% to 5% by weight, still further more preferably 0.3% to 3% by weight, calculated to the total weight of the composition.

In a preferred aspect of the present invention, the preferred surfactant of compounds a) are anionic surfactants and the total concentration of anionic surfactants is in the range of 0.1% to 10% by weight, preferably in the range of 0.2% to 8% by weight, more preferably in the range of 0.3% to 5% by weight, further more preferably 0.3% to 3% by weight, calculated to the total weight of the composition, from the viewpoint of composition stability.

Compounds According to b)

The composition of the present invention comprises one or more fatty alcohol(s) having a linear or branched, saturated or unsaturated $C_{12}$-$C_{22}$ hydrocarbon chain, and/or their mixtures, as compounds according to b).

Suitable fatty alcohols having branched or linear, saturated or unsaturated $C_{12}$ to $C_{22}$ alkyl chains are, for example, lauryl alcohol, tridecyl alcohol, myristyl alcohol, pentadecyl alcohol, cetyl alcohol, palmitoleyl alcohol, heptadecyl alcohol, stearyl alcohol, oleyl alcohol, nonadecyl alcohol, arachidyl alcohol, behenyl alcohol, and/or their mixtures.

It is preferred that one or more fatty alcohol(s) is selected from fatty alcohols having branched or linear, saturated or unsaturated $C_{14}$ to $C_{18}$ alkyl chains, preferably saturated $C_{14}$ to $C_{18}$ alkyl chains, and/or their mixtures, more preferably it is a mixture of fatty alcohols having saturated and linear $C_{16}$ and $C_{18}$ alkyl chains, from the viewpoint of conferring color intensity to hair and providing conditioning effect.

The preferred fatty alcohol is cetearyl alcohol from the viewpoint of cosmetic compatibility, conferring color intensity to hair, and providing conditioning properties.

It is preferred that the total concentration of fatty alcohols of b) is 1% by weight or more, preferably 2% by weight or more, more preferably 3% by weight or more, calculated to the total weight of the composition, from the viewpoint of conferring color intensity to hair and providing conditioning effect to the dyed hair.

It is preferred that the total concentration of fatty alcohols of b) is 20% by weight or less, preferably 15% by weight or less, more preferably 10% by weight or less, calculated to the total weight of the composition, from the viewpoint of conferring color intensity to hair, providing conditioning effect to the dyed hair, and achieving a storage stable composition.

Preferably, for attaining the above-mentioned effects, the total concentration of fatty alcohols of b) is in the range of 1% to 20% by weight, more preferably in the range of 2% to 15% by weight, further more preferably in the range of 3% to 10% by weight, calculated to the total weight of the composition.

Compounds According to c)

The composition of the present invention comprises one or more hair direct dyes selected from anionic and/or non-ionic hair direct dyes as compounds according to c).

The term anionic and/or non-ionic hair direct dye within the meaning of the present invention refers to the ionic status of the dye at the pH condition of 6 to 8.5.

It is preferred from the viewpoint of conferring color intensity to hair that the one or more hair direct dye of compounds according to c) is/are selected from non-ionic hair direct dyes. Thus, the respective dye is non-ionic at a pH range from 6 to 8.5.

All suitable dyes satisfying the definition of above may be used for the purpose of the present invention.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable non-ionic dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2- Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

However, the most preferred hair direct dyes for compounds according to c) are selected from HC Blue 18, HC Red 18, and HC Yellow 16, and/or their mixtures, from the viewpoint of color intensity.

It is preferred that the total concentration of direct dyes of c) is 0.01% by weight or more, preferably 0.02% by weight or more, calculated to the total weight of the composition, from the viewpoint of conferring sufficient color intensity to hair.

It is preferred that the total concentration of direct dyes of c) is 0.8% by weight or less, preferably 0.25% by weight or less, calculated to the total weight of the composition, from the viewpoint of cost of goods.

Preferably, for attaining the above-mentioned effects, the total concentration of direct dyes of c) is in the range of 0.01% by weight to 0.8% by weight, more preferably 0.02% by weight to 0.25% by weight, calculated to the total weight of the composition.

In one aspect of the present invention the total concentration of direct dyes selected from HC Blue 18, HC Red 18, and HC Yellow 16, and/or their mixtures, preferably is in the range of 0.01% by weight to 0.8% by weight, more preferably 0.02% by weight to 0.25% by weight, calculated to the total weight of the composition, from the viewpoint of cost of goods.

Feature According to d)

The composition of the present invention comprises one or more buffer system(s) according to d) having a buffer capacity in the range of 0.002 g equiv/L to 0.5 g equiv/L at a pH range between 6 and 8.5, the buffer capacity being measured by acid/base titration of the composition being diluted 1:10 by volume with water at 25° C. under atmospheric conditions.

The buffer capacity is determined in the following manner: 10 mL of the hair dye composition is diluted with water to 100 mL. Then the pH of the resulting solution is measured with appropriate means such as a pH electrode. A 1N aqueous solution of hydrochloric acid or sodium hydroxide is then added dropwise by titration to the solution to determine a volume of acid/base ($\times$[mL]) to decrease/increase the pH of the solution of the hair dye composition by 1 unit. The density of the hydrochloric acid/sodium hydroxide solution is assumed to be 1 g/cm$^3$, and, thus, the volume is expressed in [g] accordingly. The buffer capacity is calculated according to the following equation:

$$\text{Buffer capacity} = x[g] * 10/1000 \text{ [gram equivalent/L]}$$

It is preferred from the viewpoint of formulation freedom and conferring color intensity of hair that the buffer capacity according to d) is in the range of 0.003 g equiv/L to 0.25 g equiv/L at a pH range between 6 and 8.5, more preferably in the range of 0.003 g equiv/L to 0.1 g equiv/L, further more preferably 0.003 g equiv/L to 0.05 g equiv/L, the buffer capacity being measured by acid/base titration of the composition being diluted 1:10 by volume with water at 25° C. under atmospheric conditions.

Suitable buffer system examples for the pH range of 6 to 8.5 are:
Dibasic sodium phosphate and monobasic sodium phosphate;
Dibasic potassium phosphate and monobasic potassium phosphate;
Dibasic sodium phosphate and citric acid;
Boric acid and sodium hydroxide.

It is preferred from the viewpoint of cosmetic compatibility that the buffer system of d) is a phosphate-based buffer system. Phosphate-based buffer systems comprise at least one phosphate salt, as exemplarily shown above for the first three buffer systems. The most preferred buffer system are bibasic sodium phosphate and monobasic sodium phosphate and dibasic potassium phosphate and monobasic potassium phosphate.

Preferably, from the viewpoint of buffer capacity of phosphate buffers, the pH of the composition of the present invention is in the range of 6 to 8.

It is preferred that the total concentration of buffering salt(s) is 0.1% by weight or more, preferably 0.25% by weight or more, further more preferably 0.5% by weight or more, calculated to the total weight of the composition, from the viewpoint of providing sufficient buffer capacity.

It is preferred that the total concentration of buffering salt(s) is 10% by weight or less, preferably 8% by weight or less, further more preferably 5% by weight or less, calculated to the total weight of the composition, from the viewpoint of cosmetic acceptance.

Preferably, for attaining the above-mentioned effects, the total concentration of buffering salt(s) is in the range of 0.1% to 10% by weight, more preferably 0.25% to 8% by weight, still more preferably 0.5% to 5% by weight, calculated to the total weight of the composition.

Suitable total molar concentrations of the buffer salts are 0.01M to 0.5M.

In one aspect of the present invention, the total concentration of phosphate salts in a phosphate buffer system is in the range of 0.1% to 10% by weight, more preferably 0.25% to 8% by weight, still more preferably 0.5% to 5% by weight, calculated to the total weight of the composition.

pH Adjustment

It is to be noted from the viewpoint of adjusting the pH in the desired range between 6 and 8.5, that the skilled person will choose an appropriate acid or base based on its compatibility with the composition. Suitable acids are hydrochloric acid and phosphoric acid. Suitable bases are sodium hydroxide or potassium hydroxide.

Method of Making a Non-Oxidative Hair Dye Composition and Hair Dyeing Method

The present invention is also directed to a method of making a non-oxidative hair coloring composition comprising the steps of:
i) providing a first composition comprising one or more hair direct dyes selected from anionic and/or non-ionic direct dyes according to compound c) as defined above,
ii) providing a second composition comprising
one or more surfactant(s) according to compounds a) as defined above,
one or more fatty alcohols according to compound b) as defined above,
one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above,
iii) mixing the compositions of steps i) and ii) to yield a ready-to-use composition having a pH in the range of 6 to 8.5.

It is preferred from the viewpoint of color intensity that the ready-to-use composition comprises one or more cationic surfactant and/or cationic polymer, wherein the total equivalent molar ratio in the ready-to-use composition of cationic surfactant and/or cationic polymer to one or more hair direct dyes according to compounds c) is 15 or less, preferably 10 or less, more preferably 5 or less.

It is further preferred from the viewpoint of color intensity that the ready-to-use composition is free of cationic polymers and/or cationic surfactants.

The present invention also directed to a method for non-oxidative hair coloring comprising the steps of:
iv) applying the ready-to-use mixture as defined above onto hair for a time period of 1 min to 60 min,
v) optionally rinsing off the hair.

It is preferred from the viewpoint of conferring a high color intensity and user convenience to hair that the ready-to-use mixture in step iv) remains for a time period of 5 to 20 min on hair.

According to method step v) the ready-to-use mixture may be a leave-in composition and is not rinsed-off from hair. This is particularly preferred for costumers that desire a high degree of conditioning of their hair.

Equally suitable, the ready-to-use mixture of step v) is a rinse-off composition and is rinsed-off from hair. This is particularly preferred for customers that do not desire a weigh-down effect of leave-in compositions.

In one aspect of the aforementioned method of the present invention, the ready-to-use composition of step iv) comprises one or more cationic surfactant and/or cationic polymer, wherein the total equivalent molar ratio of cationic surfactant and/or cationic polymer to one or more hair direct dyes according to compounds c) is 15 or less, preferably 10 or less, more preferably 5 or less, from the viewpoint of enhancing color intensity on hair.

In a preferred aspect of the aforementioned method of the present invention from the viewpoint of enhancing color intensity of hair, the ready-to-use composition of step iv) is free of cationic polymers and/or cationic surfactants.

Use of the Composition

It is one object of the present invention, as defined above, that the composition of the present invention is used for enhancing uptake of anionic and/or non-ionic direct dyes according to compound c) as defined above into hair.

In one aspect of the use of the composition as defined above, the composition comprises one or more cationic surfactant and/or cationic polymer, wherein the total equivalent molar ratio of cationic surfactant and/or cationic polymer to one or more hair direct dyes according to compounds c) is 15 or less, preferably 10 or less, more preferably 5 or less, from the viewpoint of enhancing color intensity.

It is a preferred aspect of the use from the viewpoint of color uptake that for the composition as defined above, the composition is free of cationic surfactants and/or cationic polymers.

Two-Part Dyeing Composition

It is one object of the present invention, as defined above, that relates to a two-part non-oxidative dyeing composition having a part A comprising one or more anionic and/or non-ionic dyes as defined above as compound c), and a part B comprising
one or more surfactant(s) according to compounds a) as defined above,
one or more fatty alcohols having a linear or branched, saturated or unsaturated $C_{12}$-$C_{22}$ hydrocarbon chain according to compound b) as defined above,
one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above.

Parts A and B of the two-part composition are kept separate until directly prior to application onto hair.

The invention preferably is a two-part composition when incompatibilities of ingredients other than the ones defined above are expected. Such incompatibilities could arise during storage of the composition.

Kit-of-Parts

It is one object of the present invention, as defined above, that relates to a kit-of-parts comprising two compositions kept separate until directly prior to use, wherein the first separate composition comprises one or more anionic and/or non-ionic dyes as defined above as compound c), and the second separate composition comprises
- one or more surfactant(s) according to compounds a) as defined above,
- one or more fatty alcohols according to compound b) as defined above,
- one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to feature d) as defined above.

EXAMPLES

Working Comparative Examples

Hair dye compositions as shown in the Table 1 below were prepared as explained below. The obtained hair dye compositions were evaluated for buffer capacity and C* by the following method section. The results of these are all together shown in Table 1 below.

Working examples 13 to 22 are presented in table 2 by using the same methods.

Method for Preparing Hair Dye Composition

Compound c) was dissolved in water. The solution was stirred for a predetermined time to prepare a first composition. Separately, components a) and b), dibasic sodium phosphate and monobasic sodium phosphate were dissolved in water to prepare a second composition. Subsequently, the second composition was blended with the first composition and the resultant mixture was stirred for a predetermined time to obtain a hair dye composition.

TABLE 1

| | | | Working example | | | | | | Comparative example | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| | | | | | | | | % by weight | | | | | | |
| Composition | Compound (a) | Sodium cetearyl phosphate | — | 0.35 | — | 0.35 | — | 0.35 | — | 0.35 | — | 0.35 | — | 0.35 |
| | | Cetrimonium chloride | 0.35 | — | 0.35 | — | 0.35 | — | 0.35 | — | 0.35 | — | 0.35 | — |
| | Compound (b) | Cetearyl alcohol | 3.0 | 3.0 | 3.0 | 3.0 | 3.0 | 3.0 | 3.0 | 3.0 | 3.0 | 3.0 | 3.0 | 3.0 |
| | Compound (c) | HC Blue 18 | 0.035 | 0.035 | — | — | — | — | 0.035 | 0.035 | — | — | — | — |
| | | HC Red 18 | — | — | 0.035 | 0.035 | — | — | — | — | 0.035 | 0.035 | — | — |
| | | HC Yellow 16 | — | — | — | — | 0.035 | 0.035 | — | — | — | — | 0.035 | 0.035 |
| | Feature (d) | Dibasic sodium phosphate [anhydrous] | 0.97 | 0.97 | 0.97 | 0.97 | 0.97 | 0.97 | — | — | — | — | — | — |
| | | Monobasic sodium phosphate [anhydrous] | 0.19 | 0.19 | 0.19 | 0.19 | 0.19 | 0.19 | — | — | — | — | — | — |
| | | Buffer capacity [g equiv/L] | 0.003 | 0.0049 | 0.003 | 0.0049 | 0.003 | 0.0049 | 0.0008 | 0.0015 | 0.0008 | 0.0015 | 0.0008 | 0.0015 |
| pH/balance | | NaOH/HCl | | | | | | q.s. ad pH 7.5 | | | | | | |
| | | Water | | | | | | Ad 100.0 | | | | | | |
| | | C* | 5.93 | 8.88 | 16.70 | 44.30 | 20.71 | 25.04 | 2.72 | 3.48 | 13.44 | 28.69 | 18.4 | 21.30 |

TABLE 2

| | | | Working example | | | | | | | | |
|---|---|---|---|---|---|---|---|---|---|---|---|
| | | | 13 | 14 | 15 | 16 | 17 | 18 | 19 | 20 | 21 |
| | | | | | | | % by weight | | | | |
| Composition | Compound (a) | Sodium cetearyl phosphate | 0.35 | 0.35 | 0.35 | 0.35 | 0.35 | 5.0 | 0.35 | 0.35 | — |
| | | Sodium lauryl sulfate | — | — | — | — | — | — | — | — | 0.35 |

TABLE 2-continued

| | | Working example | | | | | | | | |
|---|---|---|---|---|---|---|---|---|---|---|
| | | 13 | 14 | 15 | 16 | 17 | 18 | 19 | 20 | 21 |
| | | | | | % by weight | | | | | |
| Compound (b) | Cetearyl alcohol | 3.0 | 3.0 | 3.0 | 3.0 | 3.0 | 5.0 | 3.0 | 3.0 | 3.0 |
| Compound (c) | HC Blue 18 | 0.035 | — | — | 0.035 | 0.035 | 0.8 | 0.035 | 0.035 | 0.035 |
| | HC Red 18 | — | 0.035 | — | — | — | — | — | — | — |
| | HC Yellow 16 | — | — | 0.035 | — | — | — | — | — | — |
| Feature (d) | Dibasic sodium phosphate [anhydrous] | 15.0 | 15.0 | 15.0 | 0.97 | 0.97 | 0.97 | 0.97 | — | 0.97 |
| | Monobasic sodium phosphate [anhydrous] | 3.0 | 3.0 | 3.0 | 0.19 | 0.19 | 0.19 | — | — | 0.19 |
| | Citric acid | — | — | — | — | — | — | 0.19 | — | — |
| | Sodium carbonate | — | — | — | — | — | — | — | 0.97 | — |
| | Sodium bicarbonate | — | — | — | — | — | — | — | 0.19 | — |
| | Buffer capacity [g equiv/L] | 0.044 | 0.044 | 0.044 | 0.002 | 0.0049 | 0.0037 | 0.003 | 0.0025 | 0.0038 |
| pH/ balance | NaOH/HCl | | q.s. ad pH 7.5 | | p.s. ad pH 8.5 | q.s. ad pH 6 | | q.s. ad pH 7.5 | | |
| | Water | | | | Ad 100.0 | | | | | |
| | C* | 10.38 | 51.51 | 21.93 | 11.13 | 9.91 | 12.63 | 11.12 | 18.50 | 11.36 |

| Working example 22 | |
|---|---|
| | % by weight |
| First composition | |
| Aminomethyl propanol | 5.0 |
| HC Red 18 | 2.0 |
| HC Yellow 16 | 0.5 |
| Fragrance | q.s. |
| 1,2-propylene glycol | ad 100.0 |
| Second composition | |
| Sodium lauryl sulfate | 3.0 |
| Stearyl alcohol | 2.0 |
| Dibasic sodium phosphate | 2.5 |
| Monobasic sodium phosphate | 0.3 |
| NaOH/HCl | ad pH 8.0 |
| Water | ad 100.0 |

0.5 mL of the first composition are mixed into 20 mL of the second composition to yield a ready-to-use mixture.

Example 22 is an illustration of the second object of the present invention as well as the two-part composition and the kit-of-parts.

Methods

Determination of Buffer Capacity

Buffer capacity within meaning of the present invention means a value determined by using, as a measure, the concentration of an acid required to decrease the pH of a 10% aqueous solution of a composition at 25° C. by 1 unit from the initial value thereof according to the following equation:

Buffer Capacity=$\Delta C_a/\Delta pH$ wherein Ca is an ion concentration of the acid (gram equivalent/L, abbreviated as g equiv/L).

In the examples above, the buffer capacity of each composition was determined in the following manner: 10 mL of the hair dye composition were diluted with water to 100 mL. Then the pH of the resulting solution was measured. A 1N aqueous solution of hydrochloric acid was then added dropwise by titration to the solution to determine a volume of acid (x[mL]) to decrease the pH of the solution of the hair dye composition by 1 unit. The density of the hydrochloric acid solution is assumed to be 1 g/cm$^3$, and, thus, the volume is expressed in [g] accordingly. The buffer capacity is calculated according to the following equation:

Buffer capacity=$x$[g]*10/1000[gram equivalent/L]

Hair Coloring Experiments

Yak hair was purchased from International Hair Importers, Glendale, NY, USA, as a bundle of 2 g of fibers per streak. The hair was then bleached with a commercially available bleach under the brand name Goldwell Silklift Control for 30 min at 40° C. The streaks were then shampooed and blow-dried. Then 1 g of the hair dye compositions from above were applied to bleached yak hair and left on the hair for 3 min at room temperature. The streaks were rinsed once with water at 37° C. for 1 min.

Color intensity was measured with a Datacolor 45 G instrument obtained from Datacolor Inc. Chroma according to the CIE*lab system was measured and reported above as C*. Chroma corresponds to color intensity.

The invention claimed is:
1. A non-oxidizing hair dye composition having a pH in the range of 6 to 8.5 and comprising:
   a) one or more surfactant(s),
   b) one or more fatty alcohol(s) having a linear or branched, saturated or unsaturated $C_{12}$-$C_{22}$ hydrocarbon chain, and/or their mixtures,
   c) one or more hair direct dyes which are at least one selected from the group consisting of anionic and non-ionic hair direct dyes, and
   d) one or more buffer system(s) having a buffer capacity in the range of 0.002 g equiv/L to 0.5 g equiv/L at a pH range between 6 and 8.5, the buffer capacity being measured by acid/base titration of the composition being diluted 1:10 by volume with water at 25° C. under atmospheric conditions.

2. The composition according to claim 1, wherein the surfactant of a) is at least one selected from the group consisting of anionic, cationic, amphoteric/zwitterionic, and non-ionic surfactants.

3. The composition according to claim 1, wherein the surfactant of a) is an anionic surfactant(s).

4. The composition according to claim 1, wherein the hair direct dyes are at least one selected from the group consisting of HC Blue 18, HC Red 18, and HC Yellow 16.

5. The composition according to claim 1, which comprises one or more cationic surfactant and/or cationic polymer, wherein the total equivalent molar ratio of the cationic surfactant and/or cationic polymer to one or more hair direct dyes according to compounds c) is 15 or less.

6. The composition according to claim 1, which is free of cationic polymers and/or cationic surfactants.

7. The composition according to claim 1, wherein the buffer capacity according to d) is in the range of 0.003 g equiv/L to 0.25 g equiv/L at a pH range between 6 and 8.5, the buffer capacity being measured by acid/base titration of the composition being diluted 1:10 by volume with water at 25° C. under atmospheric conditions.

8. The composition according to claim 1, wherein the buffer capacity according to d) is in the range of 0.003 g equiv/L to 0.05 g equiv/L at a pH range between 6 and 8.5, the buffer capacity being measured by acid/base titration of the composition being diluted 1:10 by volume with water at 25° C. under atmospheric conditions.

9. The composition according to claim 1, wherein the buffer system of d) is a phosphate-based buffer system.

10. The composition according to claim 1, wherein the total concentration of buffering salt(s) is in the range of 0.1% to 10% by weight, calculated to the total weight of the composition.

11. The composition according to claim 1, wherein the total concentration of fatty alcohols of b) is in the range of 1% to 20% by weight, calculated to the total weight of the composition.

12. The composition according to claim 1, wherein the total concentration of said one or more sufactans(s) a) is in the range of 0.1% to 10% by weight, calculated to the total weight of the composition.

13. The composition according to claim 1, wherein the total concentration of said one or more surfactant(s) a) is in the range of 0.3% to 3% by weight, calculated to the total weight of the composition.

14. The composition according to claim 1, wherein the total concentration of direct dyes of c) is in the range of 0.01% by weight to 0.8% by weight, calculated to the total weight of the composition.

15. A method of making a non-oxidative hair colouring composition, the method comprising:
   i) providing a first composition comprising one or more hair direct dyes which are at least one selected from the group consisting of anionic and non-ionic direct dyes according to compound c),
   ii) providing a second composition comprising
   one or more surfactant(s) according to compound a),
   one or more fatty alcohols according to compound b),
   one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to d), and
   iii) mixing the compositions of steps i) and ii) to yield a ready-to-use composition having a pH in the range of 6 to 8.5,
   wherein the compounds a), b), and c) and one or more buffer systems(s) d) are defined in claim 1.

16. The method according to claim 15, wherein the ready-to-use composition comprises one or more cationic surfactant and/or cationic polymer, wherein the total equivalent molar ratio in the ready-to-use composition of cationic surfactant and/or cationic polymer to one or more hair direct dyes according to compounds c) is 15 or less.

17. The method according to claim 15, wherein the ready-to-use composition is free of cationic polymers and/or cationic surfactants.

18. A method for non-oxidative hair colouring, the method comprising:
   iv) applying the non-oxidizing hair dye composition as defined in claim 1 onto hair for a time period of 1 min to 60 min, and
   v) optionally rinsing off the hair.

19. A kit-of-parts comprising two compositions kept separate until directly prior to use, wherein the first separate composition comprises one or more anionic and/or non-ionic dyes as compound c), and the second separate composition comprises:
   one or more surfactant(s) according to compounds a),
   one or more fatty alcohols according to compound b), and
   one or more buffer systems(s) having a buffer capacity in the range of 0.002 g equiv/L to 0.5 g equiv/L at a pH in the range between 6 and 8.5, the buffer capacity being measured by titration of the composition having 10% by weight active content at 25° C. under atmospheric conditions, according to d),
   wherein the compounds a), b), and c) and one or more buffer system(s) d) are defined in claim 1.

* * * * *